May 3, 1960 W. A. HOOGERVORST Plant Pat. 1,938
FREESIA PLANT
Filed April 17, 1959
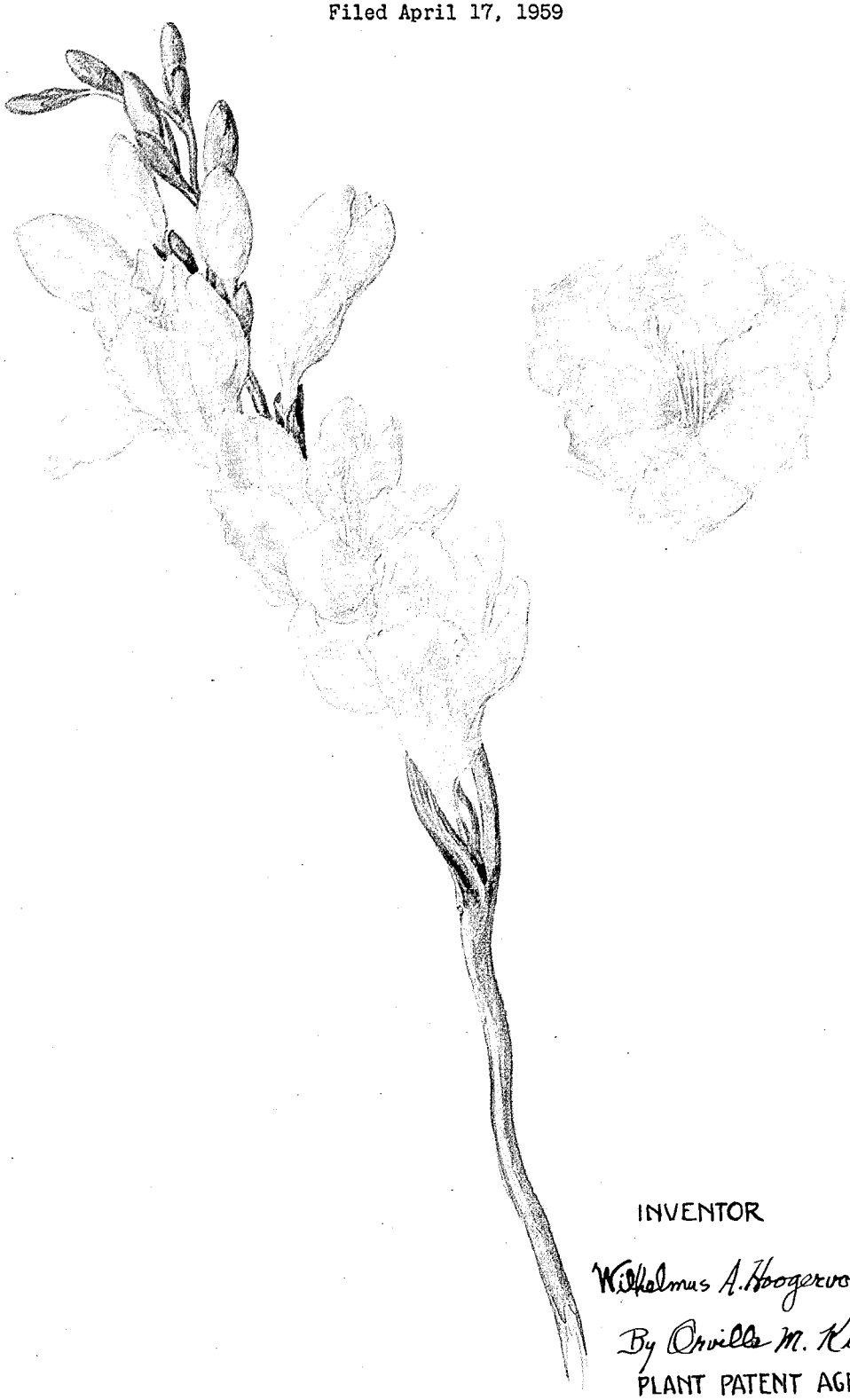
INVENTOR
Wilhelmus A. Hoogervorst
By Orville M. Kile
PLANT PATENT AGENT United States Patent Office Plant Pat. 1,938
Patented May 3, 1960

1,938

FREESIA PLANT

Wilhelmus A. Hoogervorst, Noordwyk, Netherlands, assignor to C. J. Van Bourgondien Inc., Babylon, N.Y.

Application April 17, 1959, Serial No. 807,261
1 Claim. (Cl. 47—60)

My present invention relates to improvement in yellow freesia varieties. The object of my invention is to provide a more vigorous-growing plant with flowers of a more intense yellow, and with more flowers to a spike than heretofore available.

My new freesia variety was first produced by crossing two unnamed seedling yellows, hybridized in the spring of 1951. The unnamed seedlings were of the variety Buttercup (unpatented), which is used every year. From a large quantity of bulbs planted for seed-producing purposes, this seedling stood out and was saved for asexual propagation. I reproduced this seedling asexually for five years to establish that its characteristics, as herein described, were firmly set, and very desirable in accordance with my objective. This reproduction was by separation of bulbs and was carried out at our greenhouses in Noordwyk, Holland.

There are several other yellow freesia varieties, but this one, because of its exceptional vigor, size of plant, large number of flowers to a spike, and large size and deep color of the flowers, is outstanding among yellow freesias.

The flower rachis, instead of being at right angles to the flower stem, as in other freesias, is at an angle of approximately 45 degrees to the flower stem, with the first flower about one to two inches down the stem.

The bulb is very prolific in the production of corms.

The accompanying illustrations show in approximately true colors, a spike of flowers and buds, with a separate flower in position to show its inner surface.

Following is a detailed description of the plant and flowers of this new freesia variety, with color nomenclature in accordance with the Munsel Color Chart.

*The plant*

Growth habits: This plant belongs to the class known as giant freesias, and is grown to a height of approximately 36 inches. The stem is heavier and more sturdy than is usual even with this type, and the corm production and number of flowers per spike is outstanding.

Blooming season: Unusually long, with duration of approximately six weeks.

Corms: Very round and heavy, the large bulb often producing 16 to 18 corms.

Stems: Very tall and exceptionally heavy, well-branched, and often reaching a height of 36 inches. Secondary stems are of good substance and length, with a large number of flowers on each. The main stem holds the flowers about even with the top of the foliage, the secondary flowers being lower. Color is 7.5 GY 6/8 Munsel Color Chart.

Foliage: Abundant, tall, and broader than that of most freesia varieties. About ⅝ inch in width. Average height about 36 inches. Points are long and slender, midrib prominent and of a darker green than the flower stem, the entire leaf being darker than for most varieties. Color 7.5 GY 4/4.

*The flower*

Arrangement: The flowers on a single stem or spike are borne upright, along a jointed rachis which is slightly irregular, and extends at an angle of about 45 degrees to the flower stem, with the first bloom of the series appearing about 1½ to 2 inches below the remaining flowers. The usual spike of this variety contains approximately 10 flowers, 3 or 4 of which may be open at the same time.

Sepals: Two, enclosing ovary, usually long and pointed. Approximately 7.5 GY 6/8.

Form: Perianth is long and funnel-shaped, with tube or throat slightly tapering. Petals divided deeply with a slight overlapping in a mature flower. Two or three of the petals spread at right angles, giving the flower a very broad and open look.

Size: Long, averaging 2½ inches. When fully open and spread, the flower has a width of 2¼ inches.

Fragrance: Quite pronounced and pleasing.

Petals:

*Form.*—Composed of six medium length, separate lobes gently rounded at the top but with a reflexing of three of the petals or lobes giving a rather flat appearance. Lobes are slightly overlapping.

*Color.*—The mature flower is yellow at the base; opening flower has a slightly greenish detail. The lower part of the flower up to the petals, is uniform and of a lighter shade than the petals—the color being 5Y 9/9. Where the perianth separates, there appears on the outside of the petals a pale greenish stripe, approximately 7.5 GY 9/4, which extends to the tip of the petals. All petals show a definite orange suffusion, approaching 2.5 YR 7/10, on the sides of the petals at their base where the perianth separates to form the petal, and extends almost to the tip of the petals. The inside of the flower is slightly darker than the similar outside colors, and the orange suffusion more pronounced on all the petals and extending down the perianth to the base of the flower.

Keeping qualities: Very good.

Reproductive organs:

*Stamens.*—Three. Attached to the perianth upward to the top of the throat, from which point they are free and extend about one inch.

*Filaments.*—Yellow, topped with pure white anthers.

*Pistils.*—Compound, with six white branches; situated among the stamens and arising only slightly above them; free the entire length from ovary to tip.

*Comparisons*

The two freesia varieties nearest like my new variety are Golden Daffodil (unpatented) and King of the Yellows (U.S. Plant Patent No. 448). The principal points of difference are as follows:

(1) The vigor of the plant of my new variety far exceeds that of either of the above varieties.

(2) The form of the flower is more open—not as cupped as either of the others.

(3) The color of the flower is deeper yellow and the darker splotch in the throat is distinctive.

(4) The size of flower and number of flowers to the spike is greater.

(5) The angle of the rachis to the stem of the spike is more acute.

(6) The plant is at least 6 inches taller than either of the other two.

Having thus disclosed my invention, I claim:

The new and distinct variety of giant freesia plant, approximately as herein shown and described, characterized particularly by its exceedingly vigorous, upright growth; its abundant, tall, broad foaliage; its prolific production of large corms; its long blooming season; its strong, tall, upright flower stems, which are well-branched; and its fragrant, very large, exceptionally heavy flowers of open form, good keeping quality, and yellow shades as indicated, borne on a rachis which meets the flower stem at approximately a 45-degree angle.

No references cited.